US005840008A

United States Patent [19]
Klein et al.

[11] Patent Number: 5,840,008
[45] Date of Patent: Nov. 24, 1998

[54] RADIATION EMITTING SLEEVE CATHETER AND METHODS

[75] Inventors: Enrique J. Klein; Aaron V. Kaplan, both of Los Altos, Calif.

[73] Assignee: LocalMed, Inc., Palo Alto, Calif.

[21] Appl. No.: 555,457

[22] Filed: Nov. 13, 1995

[51] Int. Cl.$^6$ .................................................. A61N 5/00
[52] U.S. Cl. ................................................. 600/3; 600/7
[58] Field of Search ........................ 600/1–8, 191–194, 600/195

[56] References Cited

U.S. PATENT DOCUMENTS

| | | | |
|---|---|---|---|
| 3,324,847 | 6/1967 | Zoumboulis | 128/1.2 |
| 3,811,426 | 5/1974 | Culver et al. | 128/1.2 |
| 4,323,055 | 4/1982 | Kubiatowicz . | |
| 4,581,017 | 4/1986 | Sahota . | |
| 4,584,991 | 4/1986 | Tokita et al. | 128/1.1 |
| 4,768,507 | 9/1988 | Fischell et al. | 128/303 R |
| 4,784,116 | 11/1988 | Russell, Jr. et al. | 600/8 |
| 4,790,315 | 12/1988 | Mueller, Jr. et al. . | |
| 4,796,629 | 1/1989 | Grayzel . | |
| 5,053,033 | 10/1991 | Clarke | 606/3 |
| 5,059,166 | 10/1991 | Fischell et al. | 600/3 |
| 5,199,939 | 4/1993 | Dake et al. | 600/3 |
| 5,213,561 | 5/1993 | Weinstein et al. | 600/7 |
| 5,302,168 | 4/1994 | Hess | 600/3 |
| 5,336,178 | 8/1994 | Kaplan et al. | 604/53 |
| 5,344,402 | 9/1994 | Crocker . | |
| 5,484,384 | 1/1996 | Fearnet | 600/3 |
| 5,503,613 | 4/1996 | Weinberger . | |
| 5,522,961 | 6/1996 | Leonhardt . | |
| 5,616,114 | 4/1997 | Thornton et al. | 600/3 |
| 5,662,580 | 9/1997 | Bradshaw et al. | 600/3 |

FOREIGN PATENT DOCUMENTS

| | | | |
|---|---|---|---|
| 0 539 136 A1 | 5/1994 | European Pat. Off. | A61N 5/10 |
| WO 96/22121 | 7/1996 | Germany . | |
| WO 94/26205 | 11/1994 | WIPO | A61F 2/06 |
| WO 95/19807 | 7/1995 | WIPO | A61N 5/00 |

OTHER PUBLICATIONS

Wiedermann et al., "Intracoronary Irradiation Markedly Reduces Restenosis After Balloon Angioplasty in a Procine Model.", 1993, Supplement to *Circulation*, vol. 88, No. 4, pt. 2, pp. I–655, *Abstract No. 3529.

Wiedermann et al., "Intracoronary Irradiation Acutely Impairs Endothelial and Smooth Muscle Function as Assessed by Intravascular Ultrasound.", 1992, Supplement to *Circulation*, vol. 86, No. 4, p. I–188, *Abstract No., 0750.

Popowski et al. "High Dose Rate Brachytherapy for Prevention of Restenosis After Percutaneous Transluminal Coronary Angiouplasty: Preliminary Dosimetric Tests of a New Source Presentation", 1995, *Int. J. Radiation Oncology Biol. Phys.*, vol. 33, No. 1, pp. 211–215.

Verin et al., "Intraarterial Beta Irradiation Prevents Neointimal Hyperplasia in a Hypercholesterolemic Rabbit Restenosis Model.", 1995, *J. Amer. College of Cardiology*, *Abstract No. 407–406.

Verin et al., "Intra–arterial Beta Irradiation Prevents Neointimal Hyperplasia in a Hypercholesterolemic Rabbit Restenosis Model.", 1995, *Circulation*, vol. 92, No. 8, pp. 2284–2290.

(List continued on next page.)

*Primary Examiner*—John P. Lacyk
*Attorney, Agent, or Firm*—Townsend and Townsend and Crew LLP

[57] ABSTRACT

The invention provides methods and devices for delivering low level radiation to inhibit neointimal hyperplasia following angioplasty or other intravascular procedures. In an exemplary method, a balloon is inflated within a stenosed region of a blood vessel to produce a treated region. The balloon is then deflated and a radioactive source within a sleeve is aligned over the deflated balloon. The balloon is again inflated at the treated region to engage the sleeve having the radioactive source against the blood vessel within the treated region for from 1 to 40 minutes to deliver a sufficient dosage of radiation to inhibit neointimal hyperplasia.

37 Claims, 6 Drawing Sheets

OTHER PUBLICATIONS

Waksman et al., "Intracoronary Radiation Before Stent Implantation Inhibits Neointima Formation in Stented Porcine Coronary Arteries", 1995, *Circulation*, vol. 92, No. 6, pp. 1383–1386.

Waksman et al., "Endovascular Low–Dose Irradiation Inhibits Neointima Formation After Coronary Artery Balloon Injury in Swine", 1995, *Circulation*, vol. 91, No. 5, pp. 1533–1539.

Wiedermann et al., "Intracoronary Irradiation Markedly Reduces Restenosis After Balloon Angioplasty in a Porcine Model.", 1994, *J. American College of Cardiology*, vol. 23, No. 6, pp. 1491–1497.

Wiedermann et al., "Intracoronary Irradiation Markedly Reduces Neointimal Proliferation After Balloon Angioplasty in Swine: Persistent Benefit a t 6–Month Follow–Up." 1995, *J. American College of Cardiology*, vol. 25, No. 6, pp. 1451–1456.

Hehrlein et al., "Low–Dose Radioactive Endovascular Stents Prevent Smooth Muscle Cell Proliferation and Neointimal Hyperplasia in Rabbits", 1995, *Circulation*, vol. 92, pp. 1570–1575.

Securities and Exchange Commission, Registration No. 333, Form 2–1, Registration Statement, *Novoste Corporation*, 7 Pages.

Brochure, "Guide for the Designer," *Uniform Tubes, Inc.*, Bulletin TDG–674, 8 Pages.

Brochure, "Rapid Strand," *Amersham Healthcare*, Medi–Physics, Inc., Bulletin TTO994A, 4 Pages.

RADIATION EMITTING SLEEVE CATHETER AND METHODS

BACKGROUND OF THE INVENTION

1. Field of the Invention

This invention relates generally to the treatment of diseased arteries. More specifically, the invention provides for the internal irradiation of a blood vessel preceding or following an angioplasty or atherectomy procedure, or the implantation of a stent.

Percutaneous transluminal angioplasty is an exemplary procedure in treating peripheral vessels or the coronary vessels surrounding the heart. During angioplasty, a catheter having an expansible distal end, usually in the form of a balloon, is positioned in a lumen of a blood vessel with the distal end disposed within a stenotic atherosclerotic region of the vessel. The expansible end is then expanded to dilate the vessel and restore adequate blood flow through the diseased region.

While angioplasty has gained wide acceptance, it continues to be limited by two major problems, abrupt closure and restenosis. Abrupt closure refers to the acute occlusion of a vessel immediately after or within the initial hours or days following the dilation procedure. This complication, occurring in approximately one in twenty cases, may result in myocardial infarction and death if blood flow is not quickly restored.

Restenosis refers to the re-narrowing of an artery after a successful angioplasty procedure. Restenosis usually occurs within the initial six months after angioplasty and afflicts approximately one in every two or three cases. Therefore, over one-third of treated patients will require additional revascularization procedures. Many different strategies have been tried to reduce the restenosis rate with mixed results, including mechanical (e.g., prolonged balloon inflations, atherectomy, laser and stenting) and pharmacologic (e.g., calcium antagonists, ace inhibitors, fish oils and steroids) approaches.

One promising new strategy for preventing restenosis is to irradiate the treated section of the coronary artery. Such procedures have been proposed in the past by placing a radiation-emitting source in the coronary artery before or after dilatation. Several of such irradiation procedures are described in, for example, U.S. Pat. Nos. 5,059,166, 5,199,939 and 5,302,168 and PCT Application WO 95/19807. Although a variety of procedures have been proposed for irradiating a treated vessel region, most of such procedures lack the ability to conveniently introduce a radiation source into a treated vessel region, to distribute the radiation source(s) uniformly within the treated vessel region, or to provide the best suited type of radiation to the vessel in the lowest effective strength, preferably over a short period of time.

For these and other reasons it would be desirable to provide methods and apparatus which would reduce or greatly eliminate such drawbacks. Such methods and devices should allow for the easy and rapid introduction and withdrawal of the radioactive source and provide for the rapid and uniform irradiation of the treated vessel region.

2. Brief Description of the Background Art

U.S. Pat. Nos. 5,199,939, 5,302,168, and PCT Application WO 95/19807 describe catheters for introducing a radioactive source to a treated portion of an artery.

U.S. Pat. No. 5,059,166 describes an intra-arterial stent incorporating a radioactive source.

Ron Waksman et al., *Endovascular Low-Dose Irradiation Inhibits Neointima Formation After Coronary Artery Balloon Injury in Swine,* Circulation, Vol 91, No 5, Mar. 1, 1995, pp 1533–1539, describe the effectiveness of low-dose intracoronary γ irradiation delivered to the site of coronary arterial overstretch balloon injury in pigs.

Joseph G. Wiedermann et al., *Intracoronary Irradiation Markedly Reduces Restenosis After Balloon Angioplasty in a Porcine Model,* JACC, Vol 23, No 6, May 1994, pp 1491–8, describe a study for evaluating the effects of intracoronary γ irradiation on neointimal proliferation after overstretch balloon angioplasty in swine.

Joseph G. Wiedermann et al., *Intracoronary Irradiation Markedly Reduces Neointimal Proliferation After Balloon Angioplasty in Swine: Persistent Benefit at 6-Month Follow-Up,* JACC, Vol 25, No. 6, May 1995, pp 1451–6 describe the long-term efficacy of intracoronary γ irradiation for limiting neointimal proliferation after overstretch balloon angioplasty in a porcine model of restenosis.

Vitali Verin et al., *Intraarterial Beta Irradiation Prevents Neointimal Hyperplasia in a Hypercholesterolemic Rabbit Restenosis Model,* JACC (Special Issue), February 1995, Abstract, describe the use of Intraarterial beta irradiation to reduce restenosis following balloon angioplasty.

Youri Popowski et al., *High Dose Rate Brachytherapy for Prevention of Restenosis After Percutaneous Transluminal Coronary Angioplasty: Preliminary Dosimetric Tests of a New Source Presentation,* Int. J. Radiology Oncology Bio. Phys., Vol. 33, No. 1, pp 211–215, 1995 describe a standard angioplasty balloon having beta emitting radioactive yttrium-90 wires within its central lumen.

Ron Waksman et al., *Intracoronary Radiation Before Stent Implantation Inhibits Neointimal Formation in Stented Porcine Coronary Arteries,* Circulation, Vol 92, No 6, Sept. 15, 1995, pp 1383–1386, describe the effectiveness of intracoronary γ and β irradiation delivered to the site of coronary arterial overstretch balloon injury in pigs.

Christoph Hehrlein et al., *Low-Dose Radioactive Endovascular Stents Prevent Smooth Muscle Cell Proliferation and Neointimal Hyperplasia in Rabbits,* Circulation, Vol. 92, No. 6, Sep. 15, 1995, pp. 1570–1575 describe the use of stents to deliver mostly β radiation to a treatment region.

Vitali Verin et al., *Intraarterial Beta Irradiation Prevents Neointimal Hyperplasia in a Hypercholesterolemic Rabbit Restenosis Model,* Circulation, Vol. 92, No. 8, Oct. 15, 1995, pp. 2284–2290, describe the use of β-emitting coils inside a centering balloon to deliver radiation.

The complete disclosures of all these references are herein incorporated by reference.

SUMMARY OF THE INVENTION

The invention provides devices and methods for performing angioplasty, and more particularly for internally irradiating a treated vessel region following balloon dilatation with an angioplasty balloon catheter used in the treated region. To internally irradiate the vessel, the invention provides a radiation-emitting device for use in combination with an angioplasty or PTCA balloon catheter or the like (hereinafter "balloon catheter"). The device includes one or more radioactive sources and structure for longitudinally and circumferentially aligning the radioactive source(s) over the balloon on the balloon catheter. In this way, the radioactive source(s) can be introduced to the treated region of the vessel, preferably in cooperation with the same balloon catheter previously employed to perform the angioplasty procedure.

The radioactive source(s) will preferably emit gamma (γ) or beta (β) radiation, with the preferred being β radiation. Exemplary of β-emitting sources include $^{90}$Strontium and $^{90}$Yttrium. Exemplary γ-emitting sources include $^{125}$Iodine and $^{192}$Iridium which emits both γ and β radiation. Preferred is use of $^{90}$Strontium as a β-emitter. The radioactive source (s) will preferably comprise a plurality of discrete elements, such as, for example, seeds, elongate strips, ribbons, wires, ribs, and the like. The aligning structure holds the radiation elements together in a desired pattern or distribution, with the radiation elements being longitudinally and circumferentially aligned over the balloon when inflated.

In a preferable embodiment, the structure comprises a radially expansible sleeve having an internal lumen for receiving the balloon. In this way, the balloon can be received within the sleeve and expanded to both radially expand the sleeve and to uniformly position the radioactive source in apposition to the vessel walls. The sleeve can be configured in a variety of ways to be radially expansible including, providing a plurality of axial splits along the sleeve, forming the sleeve at least partially of an elastomeric material or a mesh, providing the sleeve with folds, and the like. Other suitable structures include cages, flexible elements aligned over the balloon, coils, and the like.

The invention further provides an exemplary radiation-emitting sleeve catheter (RESC) having a shaft with a proximal end and a distal end. A radially expansible sleeve is disposed at the distal end of the shaft and includes an internal lumen for receiving a balloon on a balloon catheter. At least one radioactive source is provided and is secured to the radially expansible sleeve. In this manner, the RESC can be used in combination with a balloon catheter to radioactively treat a vessel. Following angioplasty with the balloon catheter, the sleeve is aligned over the balloon at the treatment site. The balloon is then inflated to radially expand the sleeve and to place the radioactive source adjacent the treated vessel walls.

In one preferable aspect, the radioactive source includes a plurality of elongate elements that are substantially uniformly distributed over the sleeve. The elements will preferably be axially aligned with the internal lumen of the sleeve and will each have a length in the range from 15 mm to 45 mm. Alternatively, one or more elongate elements that are substantially uniformly distributed over the sleeve will have a spiral configuration such that when the sleeve is collapsed, the spiral elements will nest next to each other.

In one particular aspect, the sleeve includes at least one perfusion lumen for providing blood perfusion past the balloon when inflated. Such a perfusion lumen is desirable during extended radiation treatments, such as those exceeding about three minutes. In a further particular aspect, a therapeutic drug is included in or introduced through the sleeve to provide drug therapy to the vessel during the radiation treatment. In another aspect, the sleeve is provided with a port for introducing the balloon into the sleeve in a "rapid exchange" manner. In still a further aspect, at least a portion of the shaft is constructed of a push rod surrounded or partially surrounded by a polymer tube to provide enhanced pushability to the catheter.

The invention provides an exemplary method for performing angioplasty. According to the method, a balloon is inflated within a stenosed region of a blood vessel to provide treatment. The balloon is then deflated and a radioactive source is aligned over the deflated balloon. The balloon is then reinflated to engage the radioactive source against or in close proximity to the luminal wall of the treated region of the vessel. Usually, the radioactive source will directly engage the luminal wall, although there may be portions of the catheter or other structure, such as material encapsulating the radioactive source, between the source and the wall.

In one preferred aspect, the deflated balloon is withdrawn from the blood vessel following angioplasty, and the radially expansible sleeve with the radioactive source is loaded over the shaft of the deflated balloon. After placement of the sleeve over a proximal portion of a balloon shaft, the deflated balloon is then reintroduced to the treated region of the blood vessel. The sleeve with its radioactive source is then advanced and aligned over the balloon, after which the balloon is reinflated to bring the radioactive source into apposition with the vessel wall. Alternatively, the balloon catheter may be pre-loaded with the sleeve prior to the angioplasty procedure. Following balloon deflation, the sleeve is distally advanced to align the sleeve over the balloon. The deflated balloon is preferably withdrawn from the blood vessel and reintroduced to the blood vessel with the assistance of a guidewire as is well known the medical literature.

The radioactive source will usually be activated so as to supply a total dose of about 6 Gy to 20 Gy, more preferably from about 10 Gy to 18 Gy, to the treated region over the duration of the procedure. In one aspect, the radioactive source will be maintained in the treated region for a period from about 1 minute to 40 minutes, more preferably from about 2 minutes to 3 minutes. For extended irradiation treatments of more than a 3 minute duration, particularly when treating diseased coronary arteries, the method will preferably include the step of providing blood flow past the reinflated balloon to provide adequate blood perfusion to the distal tissue.

DESCRIPTION OF THE SPECIFIC EMBODIMENTS

Figure 1:
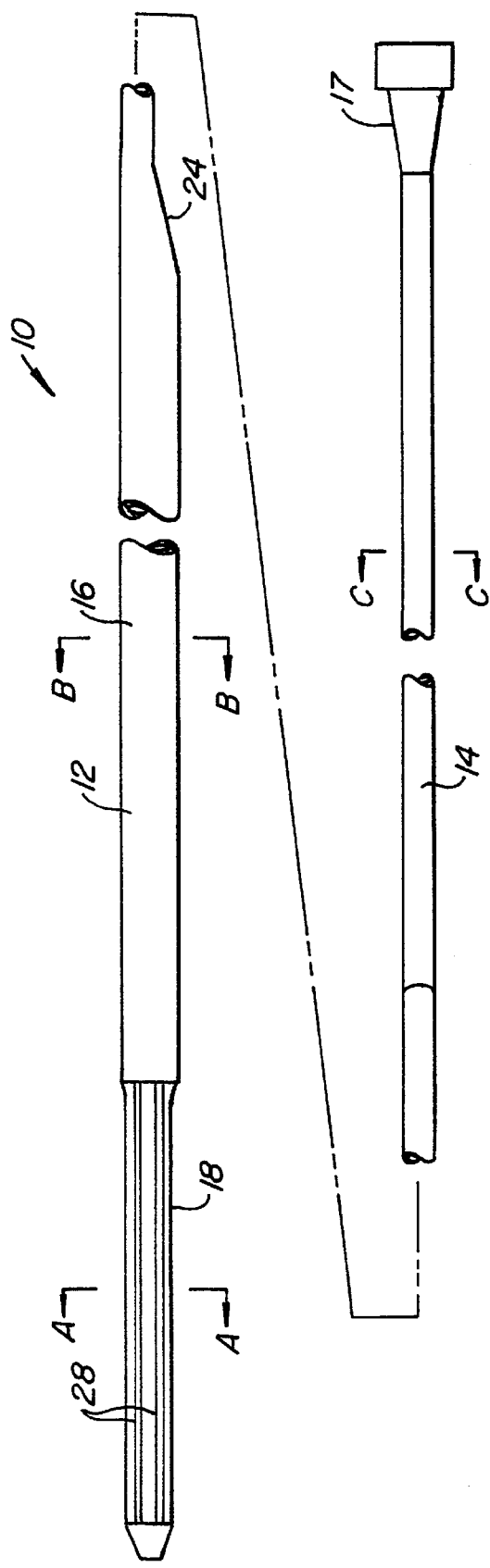
FIG. 1 is a side view of an exemplary RESC according to the present invention.

The invention provides apparatus and methods for performing angioplasty, and particularly for the internal irradiation of the treated vessel, post-dilatation. Apparatus of the invention include both a balloon catheter and a radioactive source secured within a radiation-emitting sleeve catheter (RESC). With such a configuration, the RESC having the radioactive source may be aligned over the balloon so that inflation of the balloon will place the radioactive source in apposition with a treatment region of the vessel previously dilated by the balloon.

Most commercially available balloon catheters may be used in combination with the invention. These include, for example, balloon catheters available from Advanced Cardiovascular Systems, Inc., Temecula, Calif. Such balloon catheters, which are well described in the medical literature, include an elongate catheter body and a balloon attached near a distal end of the catheter body.

Radioactive sources of the present invention include radioactive materials or radioisotopes emitting gamma ($\gamma$) and beta ($\beta$) radiation and sometimes a combination of both. Preferred radioisotopes include $^{192}$Iridium (half life of 74.2 days) emitting a spectrum of $\gamma$ plus $\beta$ radiation, $^{125}$Iodine (half life of 59.6 days) emitting $\gamma$ radiation, $^{90}$Strontium (half life of 28.1 years) and $^{90}$Yttrium (half life of 64.1 hours), both emitting $\beta$ radiation only. $^{90}$Strontium, which decays to $^{90}$Yttrium, may be a particularly attractive radioactive source in that both isotopes together, when reaching equilibrium, will emit $\gamma$ radiation on a 1 to 1 activity basis, with the $^{90}$Strontium emitting low energy radiation (maximum of 0.54 Mev) and the $^{90}$Yttrium emitting high energy radiation (maximum of 2.27 Mev). As the short lived $^{90}$Yttrium decays to $^{90}$Zirconium, it is replenished by the decay of the long lived $^{90}$Strontium.

Such radioactive sources will be activated to levels suitable for the delivery of a predetermined dose of radiation to the treatment region of the vessel wall of about 6 Gray (Gy) to 20 Gy, more preferably from about 10 Gy to 18 Gy. Depending on the source, the time since its activation, and the geometrical arrangement of the source within the diseased vessel, the irradiation will be delivered in about 1 minute to 40 minutes, and more preferably from about 2 minutes to 3 minutes.

While gamma and beta radiation have shown similar results for the inhibition of neointimal hyperplasia in animal models, with comparable activation levels and total tissue dose, these two types of radiation are substantially different from each other. Gamma rays consist of high-energy photons with no electric charge and having high penetration powers, of the order of several centimeters in lead. Beta radiation, on the other hand consists of either electrons or positrons having a negative or positive charge, respectively, and can penetrate, for example, a few millimeters of aluminum or a few centimeters of acrylic polymer.

The radioactive source may be secured within a sleeve that is placed over the balloon in a variety of manners, with an important feature being that the radioactive source be aligned over the balloon so that upon inflation of the balloon, the radioactive source will be positioned in apposition to the treated vessel wall. Further, the radioactive source secured within the sleeve will preferably be aligned over the balloon so that when the balloon is inflated, the radioactive source is substantially uniformly distributed over the treatment region of the vessel wall to uniformly irradiate the vessel wall. In this manner, since the radioactive source is positioned in such close proximity to the vessel wall, the radioactive elements may need to be energized to lesser initial activity levels than if they were located in the center of the vessel. Furthermore, when using a non-implantable radioactive source with a diameter substantially smaller than the vessel lumen, as proposed in the prior art, there is no assurance that the radioactive source will be centrally located in the vessel lumen, thus leading potentially to a non-uniform radial distribution of the radiation in the diseased vessel. This non-uniformity is particularly detrimental when using $\beta$ radiation which is markedly attenuated by substances such as blood, contrast agent, or polymeric materials surrounding the radiation source, therefore exposing different sectors of the arterial tissue surrounding the lumen to substantially different levels of irradiation.

Typically, the RESC, with the activated and sealed radiation source built into the distal end, will be appropriately shielded for the safety of the catheterization laboratory personnel and the patient. In the case of $\gamma$ radiation, the shielding would comprise a substantial lead or depleted uranium enclosure, and in the case of $\beta$ radiation of a similarly bulky polymer enclosure, usually an acrylic polymer or the like, surrounded by an additional lead or the like shield, to stop the electromagnetic radiation (also called "Bremsstrahlung") generated as the $\beta$ particles collide with the atoms in the polymer, as is common practice when handling such radiation sources.

Another consideration in the selection of the radiation-emitting source material will be the half-life of its decay process. Radioisotopes with half-lives of the order of months and years will have a much longer useful shelf-life than other radioisotopes having half-lives on the order of only a few hours, in which case the time between their activation in a reactor and their use in the catheterization laboratory becomes of critical importance. On the other hand, such short half-life materials lend themselves to much easier disposal than those having the longer decay periods.

The radioactive source will usually comprise a plurality of discrete elements that are held in place by the RESC. The discrete elements may comprise, for example, seeds, elongate ribs, ribbons, wires, and the like. The discrete elements may be attached to or integrally formed within the RESC in a sealed arrangement.

The RESC will preferably have a distal portion which is radially expansible so that upon inflation of the balloon, the radioactive source will be radially expanded toward the vessel walls. The distal portion can be fashioned to be radially expansible by including in its construction materials such as an elastomer, a mesh, a folded material, and the like, or constructing the distal portion out of a non-distensible material having an appropriate slitting pattern.

Referring now to FIG. 1 an exemplary embodiment of a radiation-emitting sleeve catheter (RESC) 10 will be described. The RESC 10 is constructed of a catheter body 12 having a proximal portion 14, a central portion 16, and a distal portion 18. The catheter body 12 will have a length depending on its desired use. Typically, the length will be from about 40 cm to 150 cm. The length of the distal portion will be at least long enough to cover the balloon. The outer diameter of the catheter body will usually be between about 1.4 mm and 2.3 mm, more usually being between about 1.6 mm and 2.0 mm. The catheter body 12 may be constructed of materials as described in co-pending U.S. application Ser. No. 08/222,143, filed May 1, 1994 (Attorney Docket No. 15509-2-2), the complete disclosure of which is herein incorporated by reference.

Figure 1A:
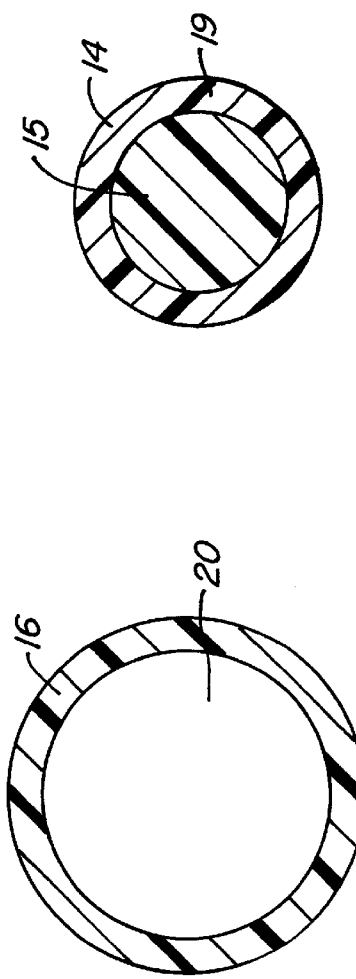
FIGS. 1A–1C are cross-sectional views of the RESC of FIG. 1 taken along lines A—A through C—C, respectively.
Figure 1B:
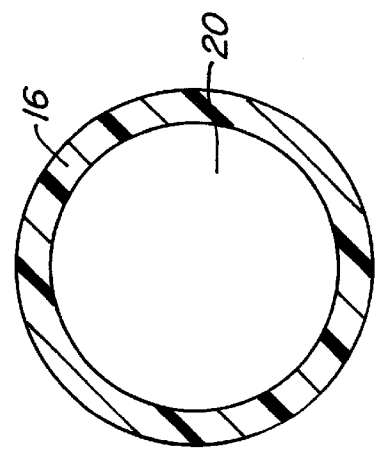
Figure 1C:
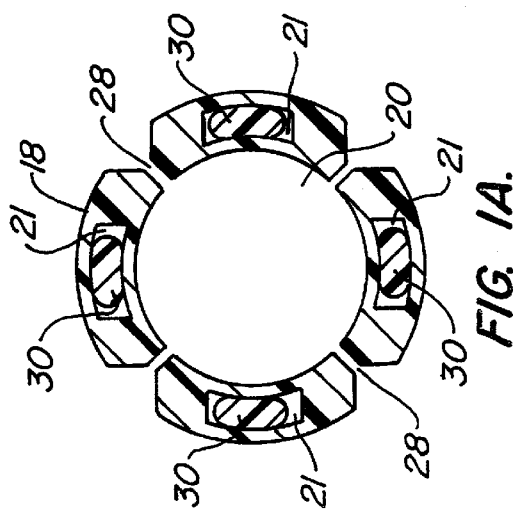

The proximal portion 14 is preferably constructed of a steel push rod 15 within a polymer sheath 19 as shown in cross-sectional view in FIG. 1C. Push rod 15 provides sufficient longitudinal stiffness for pushing RESC 10 into the vascular anatomy. A hub 17 is attached to a proximal end of the push rod. The central portion 16 is shown in cross-sectional view in FIG. 1B and is preferably constructed of a single lumen polymer tube (with or without stiffening elements such as braided steel wires or wire coils) that is attached to or integrally formed with the proximal portion 14. Extending through the central portion 16 is a central lumen 20 which includes a port 24 through which a balloon catheter may be introduced into the central lumen 20.

The distal portion 18 is shown in cross-sectional view in FIG. 1A and includes a plurality of axial slits 28 that allow the distal portion 18 to be radially expanded upon inflation of the balloon on the balloon catheter. The axial slits 28 are preferably axially aligned with the balloon on the balloon catheter. For most procedures, the axial slits 28 will allow the distal portion 18 to be radially expanded so as to engage the walls of the vessel, with the outside diameter of the distal portion usually being in the range from about 2 mm to 5 mm when radially expanded.

The distal portion 18 includes a plurality of outside lumens 21 into which a plurality of elongate radioactive elements 30 may be introduced. The elements may be constructed, for example, of materials such as those described in Youri Popowski et al., *High Dose Rate Brachytherapy for Prevention of Restenosis After Percutaneous Transluminal Coronary Angioplasty: Preliminary Dosimetric Tests of a New Source Presentation*, Int. J. Radiology Oncology Bio. Phys., Vol. 33, No. 1, pp 211–215, 1995; or Ron Waksman et al., *Intracoronary Radiation Before Stent Implantation Inhibits Neointimal Formation in Stented Porcine Coronary Arteries*, Circulation, Vol 92, No 6, Sep. 15, 1995, pp 1383–1386, the disclosures of which have previously been incorporated by reference. In some cases, the elements 30 may have sufficient transverse flexibility and longitudinal stiffness to provide rigidity to the distal portion of catheter during tracking through the vascular anatomy. optionally, stiffening elements, such as metal bars, may be placed within some of the lumens 21 as described in, for example, U.S. Pat. application Ser. No. 08/222,143 (Attorney Docket No. 15509-2-2), previously incorporated by reference.

Although shown with four radioactive elements 30, the RESC 10 can be provided with more than four elements, with each of the elements 30 preferably being equally spaced apart. In this manner, when the distal portion 18 is radially expanded, the radioactive elements 30 are equally spaced over the treatment region of the vessel to provide a substantially uniform radiation treatment of the vessel wall. This can be most advantageously attained by using an offset slit pattern as taught in co-pending U.S. Pat. application Ser. Nos. 08/241,428, filed May 11, 1994, and 08/325,958, filed Oct. 20, 1994 (Attorney Docket Nos. 15509-2-3 and 15509-13, respectively), hereby incorporated in their entirety by reference. While radioactive elements 30 in lumens 21 are shown aligned substantially with the axis of the RESC 10, it is envisaged that radioactive elements 30 and lumens 21 may have a helical construction (not shown) allowing for a different distribution of the radioactive elements 30 in the lumen of the vessel when the elements 30 are deployed.

Another particular advantage of RESC 10 is that the radioactive elements 30 may be placed in close proximity to the vessel wall. In this way, radioactive elements with lower radioactive activation levels can be provided. In another advantage, the radioactive elements are uniformly distributed against the treated region, both longitudinally and circumferentially. This, in turn, allows for a more uniform radiation treatment of the vessel. A further advantage of RESC 10 is that one size of RESC 10 can be employed to treat vessels of various sizes. To irradiate a treatment region, the same balloon catheter used to perform angioplasty in the diseased region is employed to radially expand RESC 10. In this way, proper expansion is generally assured since the same balloon employed for the primary procedure is also used to deploy the radioactive elements 30.

Figure 2:
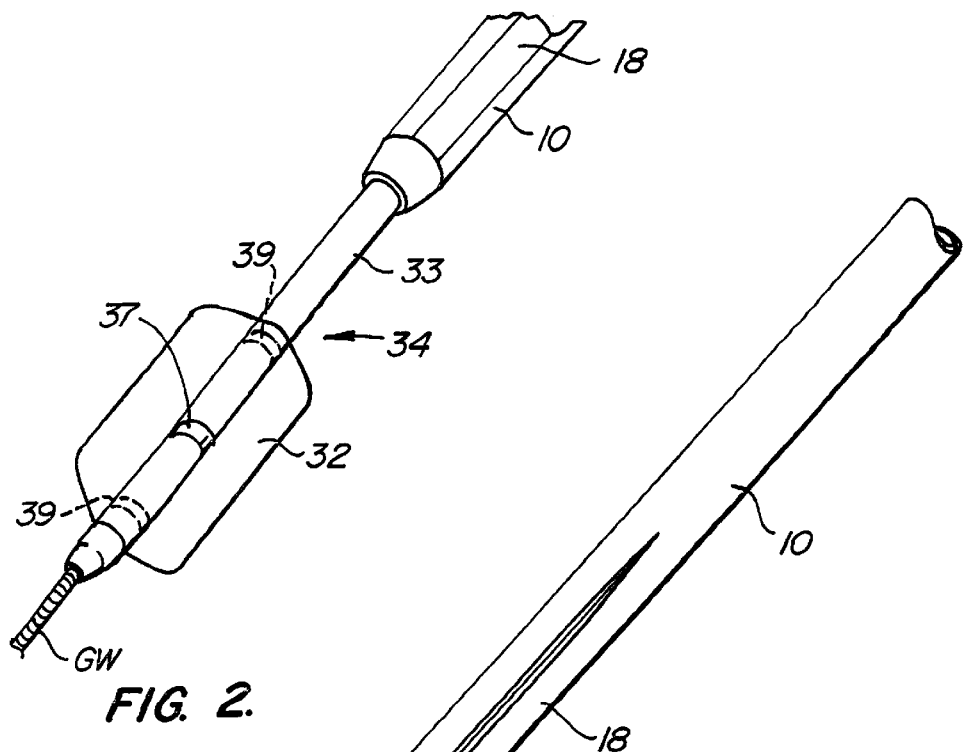
FIG. 2 is a perspective view of a distal end of the RESC of FIG. 1 placed over a balloon catheter according to the invention.
Figure 3:
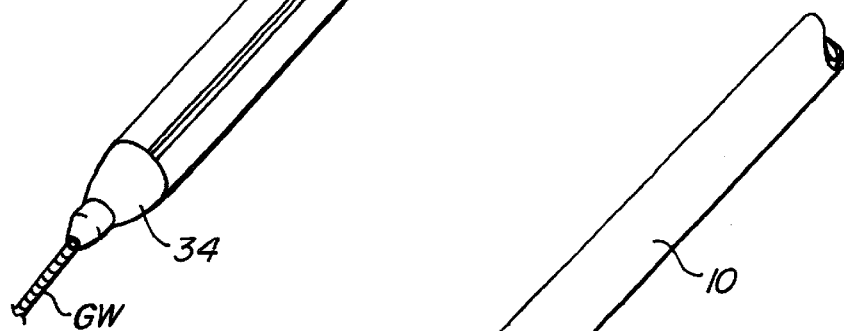
FIG. 3 is a perspective view of the distal end of the RESC of FIG. 1 when aligned over the balloon catheter of FIG. 2 according to the invention.
Figures 4, 4A:
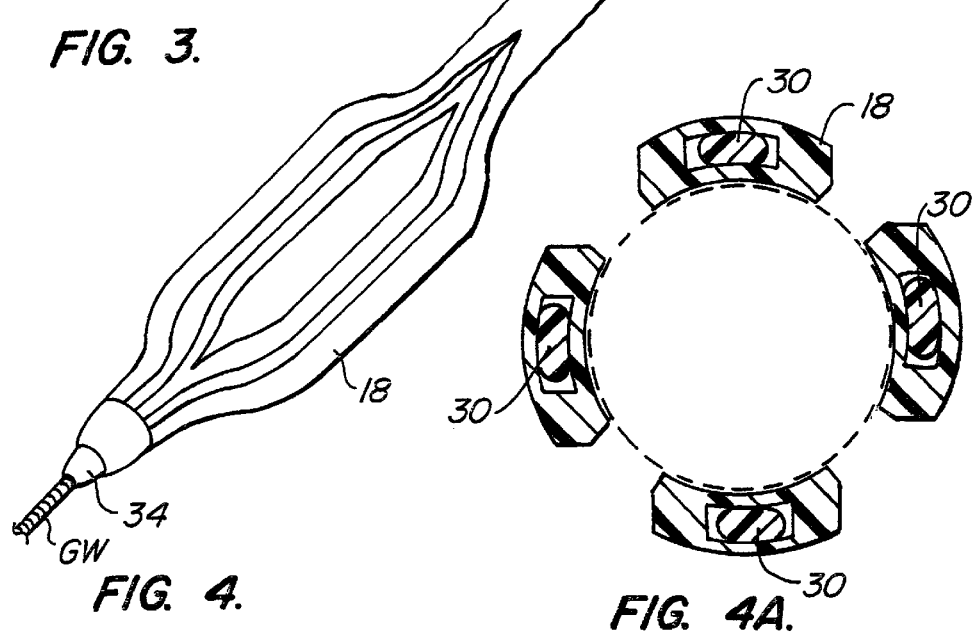
FIG. 4 illustrates the distal end of the RESC of FIG. 1 when radially expanded by the balloon catheter of FIG. 2 according to the present invention.
FIG. 4A is a cross-sectional view of the radially expanded distal end of the RESC of FIG. 4.

Cooperation of RESC 10 with a balloon catheter 34 having a shaft 33 and a balloon 32 will be described with reference to FIGS. 2–4. RESC 10 is sized so that it may be axially advanced over the shaft 33 as illustrated in FIG. 2. With the balloon 32 deflated, RESC 10 may be advanced to position the distal portion 18 over the balloon 32 as shown in FIG. 3. With RESC 10 in place, the balloon 32 is inflated to radially expand the distal portion 18 as shown in FIG. 4. As best shown in FIG. 4A, inflation of the balloon 32 will move the elements 30 radially outward so that they may engage the vessel wall.

To fluoroscopically align the angioplasty balloon with the radioactive expansible portion of RESC 10, it may be desirable to provide spaced apart markers (not shown) on RESC 10 as disclosed in U.S. Pat. No. 5,336,178, herein incorporated by reference, and co-pending U.S. Pat. application Ser. No. 08/222,143 (Attorney Docket No. 15509-2-2), previously incorporated by reference, and a central marker 37 (see FIG. 2) on balloon catheter 34. In this manner, central marker 37 may be positioned between the spaced apart markers on the RESC 10 to align the RESC 10 with the central marker 37 on balloon catheter 34. Alternatively, or in addition to the spaced-apart markers described above, it may be desirable to provide end marker pairs 50, 52 on RESC 10 (FIGS. 5 and 6) to indicate the ends of the radioactive elements 30 of RESC 10. Such end markers on the RESC 10 may then be aligned with the central marker 37 on the balloon catheter by visually centering the central marker 37 between the RESC end marker pairs. A third alignment scheme would involve aligning the RESC end marker pairs with widely spaced apart markers 39 (shown in phantom line in FIGS. 2 and 6) on the balloon catheter shaft indicating the ends of the cylindrical portion of the balloon. These marker schemes and alignment methods may be particularly advantageous when using β radiation since the β radiation from the source will be absorbed by the surrounding tissue and will not interfere with or be visible in the fluoroscopic image. On the other hand, when using a source emitting γ radiation, there may no longer be a need for additional markers on the RESC 10, since the source would absorb the X-radiation from the fluoroscope rendering the source itself radiopaque and thus fluoroscopically visible. The radioactive elements themselves would therefore provide a natural visualization means enabling centering with a central balloon marker 37 or spaced-apart balloon markers 39, using standard catheterization laboratory fluoroscopy methods.

Figure 5:
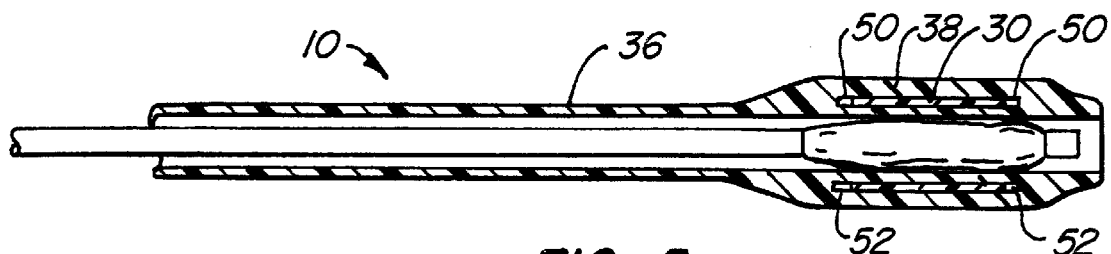
FIG. 5 illustrates a cutaway side view of one embodiment of a radially expansible sleeve having a radioactive source according to the present invention.
Figure 6:
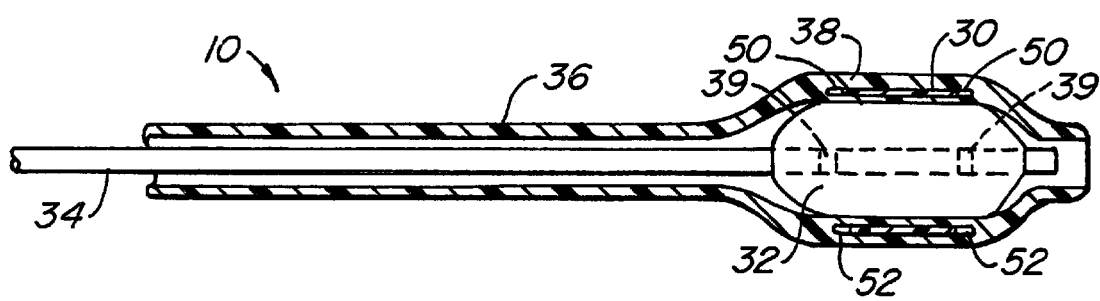
FIG. 6 illustrates the sleeve of FIG. 5 being radially expanded by a balloon.
Figure 7:
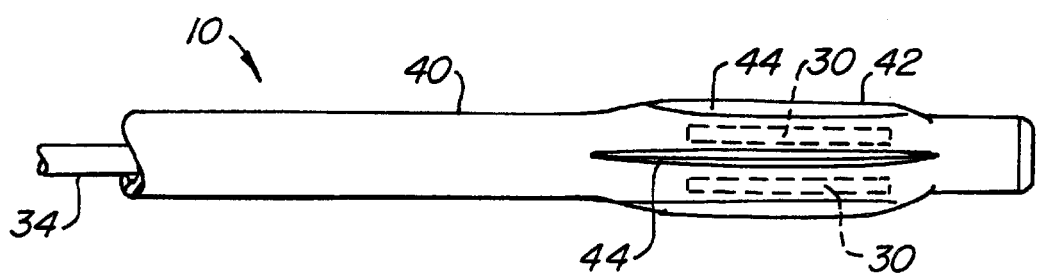
FIG. 7 illustrates a side view of an alternative embodiment of a radially expansible sleeve according to the present invention.
Figure 8:
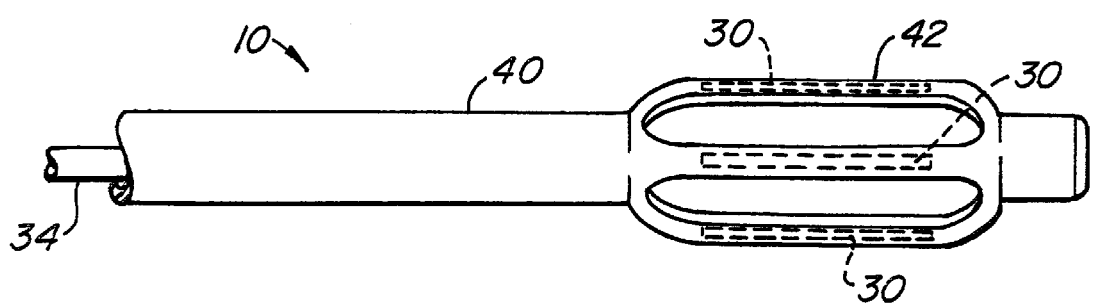
FIG. 8 illustrates the sleeve of FIG. 7 in a radially expanded state.

Alternative embodiments of RESCs are illustrated in FIGS. 5–12 and are constructed essentially identical to RESC 10 of FIG. 1 except for the construction of the distal portion 18. Referring first to FIGS. 5 and 6, an alternative embodiment of a distal portion 36 will be described. The distal portion 36 includes a radially expansible region 38 having the radioactive elements 30. As best shown in FIG. 6, when the balloon 32 is inflated while within the expansible region 38, the walls of the expansible region 38 radially expand and become thinner. Radial expansion of the region 38 radially translates the elements 30 until the expansible region 38 comes in contact with the vessel wall. The expansible region 38 is constructed of an elastomeric material, such as a medical grade synthetic rubber, Santoprene™ (Advanced Elastomeric Systems) or a thermoplastic elastomeric polyurethane sold under the trademark Tecoflex™ by Thermetics, Inc. or Kraton™ by Shell Chemical Co. Construction of the distal portion 36 is described in greater detail in co-pending U.S. Pat. application Ser. No. 08/325,958 (attorney docket no. 15509-13), previously incorporated herein by reference. Optionally, as further described in U.S. Pat. application Ser. No. 08/325,958 the expansible region 38 can be constructed to include a porous matrix material containing a drug interspersed therein. In this way, delivery of a variety of therapeutic agents can be provided while simultaneously providing radiation therapy. Referring to FIGS. 7 and 8, a further alternative embodiment of a distal portion 40 of RESC 10 will be described. The distal portion 40 includes a radially expansible region 42 having a plurality of folds 44. The radially expansible region 42 can be constructed of any non-compliant polymeric material having folds or pouches formed integrally with the polymeric material as taught in co-pending U.S. Pat. application No. 08/401,541, filed Mar. 10, 1995 (Attorney Docket No. 15509-7-2), herein incorporated by reference. The radially expansible region 42 is radially expanded by the balloon catheter 34 as shown in FIG. 8. As the balloon catheter 34 is inflated, the folds 44 expand to increase the surface area of the expansible region 42 and allow the radioactive elements 30 (shown in phantom line) to move radially outward toward the vessel wall.

Figure 9:
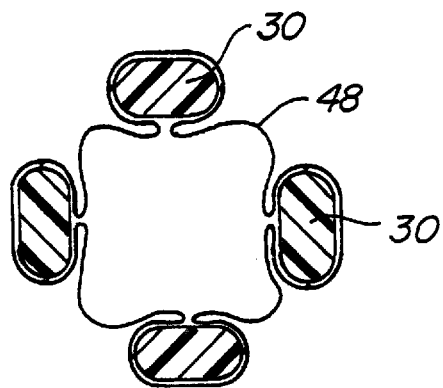
FIG. 9 illustrates a cross-sectional view of a further alternative embodiment of a radially expansible sleeve having a radioactive source according to the present invention.
Figure 10:
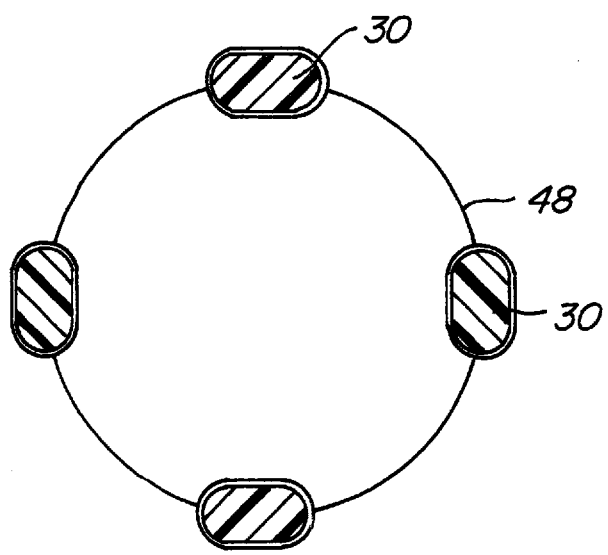
FIG. 10 illustrates the sleeve of FIG. 9 when radially expanded.

Referring to FIGS. 9 and 10, still a further alternative embodiment of a distal portion 46 of the RESC 10 will be described. The elements 30 are held within a sleeve 48 which is folded to hold the elements 30 close together as illustrated in FIG. 9, When the balloon is expanded, the sleeve 48 unfolds as illustrated in FIG. 10.

Figure 11:
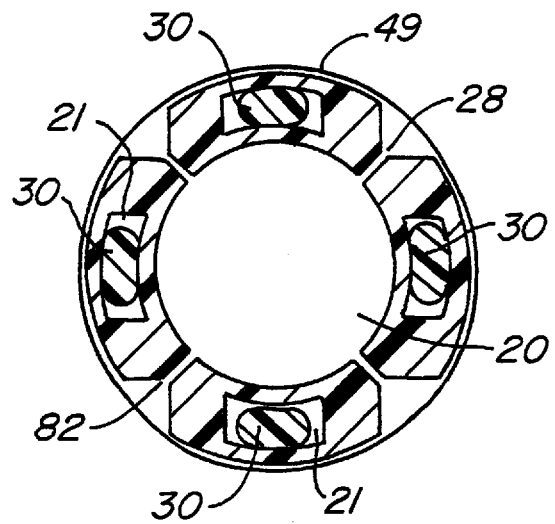
FIG. 11 illustrates the radiation emitting sleeve catheter of FIG. 1A surrounded by an elastomeric tubular sheath.
Figure 12:
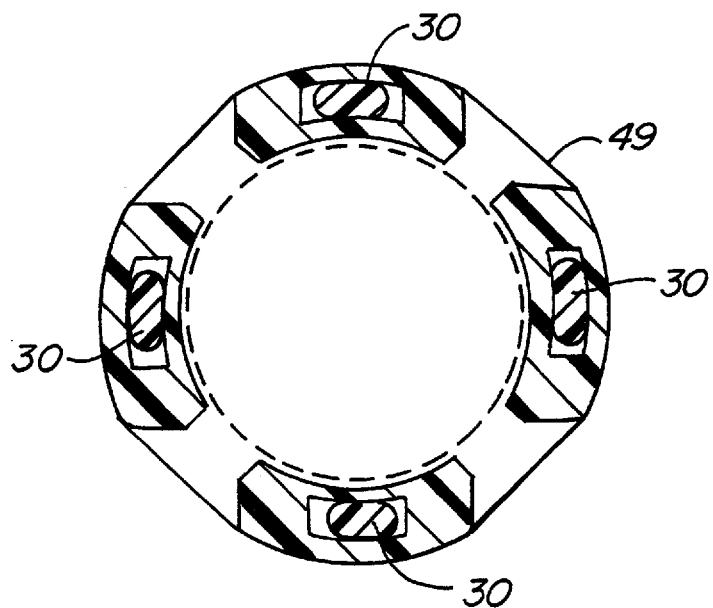
FIG. 12 illustrates the radiation emitting sleeve catheter of FIG. 11 when radially expanded.

Another alternative configuration of a distal portion 46 of RESC 10 is shown in FIGS. 11 and 12 wherein the portion of the catheter having slits 28 is enclosed by an elastomeric tubular sheath 49. Sheath 49 may be constructed of an elastomeric material, such as a medical grade synthetic rubber, Santoprene™ (Advanced Elastomeric Systems) or a thermoplastic elastomeric polyurethane sold under the trademark Tecoflex™ by Thermetics, Inc. or Kraton™ by Shell Chemical Co. One advantage of sheath 49 is that it will preclude a "winged" deflated balloon from getting caught in slits 28 when moving the balloon catheter relative to RESC 10. Also, the elastomeric tubular sheath 49 would urge radioactive elements 30 and distal portion 18 of catheter body 12 to contract uniformly following deflation of the balloon.

Other embodiments of radially expansible regions that would be capable of including a radioactive source according to the invention are described in co-pending U.S. Pat. application Ser. No. 08/222,143 (Attorney Docket No. 15509-2-2), filed May 1, 1994, previously incorporated by reference. For example, described in U.S. Pat. application Ser. No. 08/222,143 is a distal portion having a plurality of elongate slits formed in a webbed pattern and which can optionally be provided with an infusion array for delivering an agent to the treatment region. The webbed pattern allows the radioactive material to be uniformly distributed against the treatment region of the vessel wall.

Figure 13:
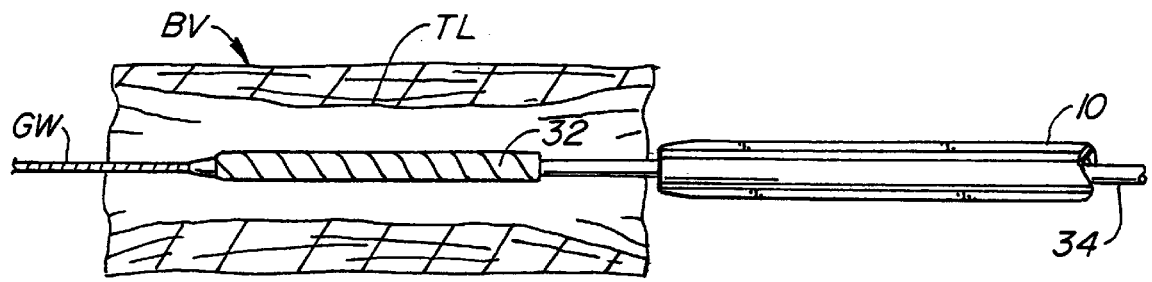
FIGS. 13–15 illustrate an exemplary method irradiating an angioplasty treatment site by aligning a radioactive, radially expansible sleeve over a balloon and inflating the balloon.
Figure 14:
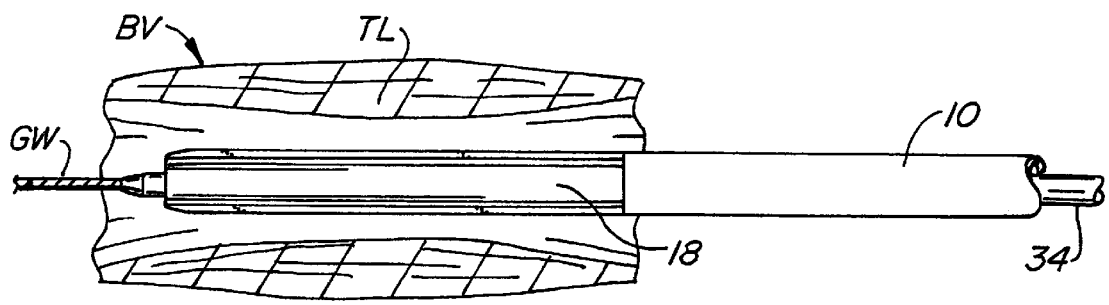
Figure 15:
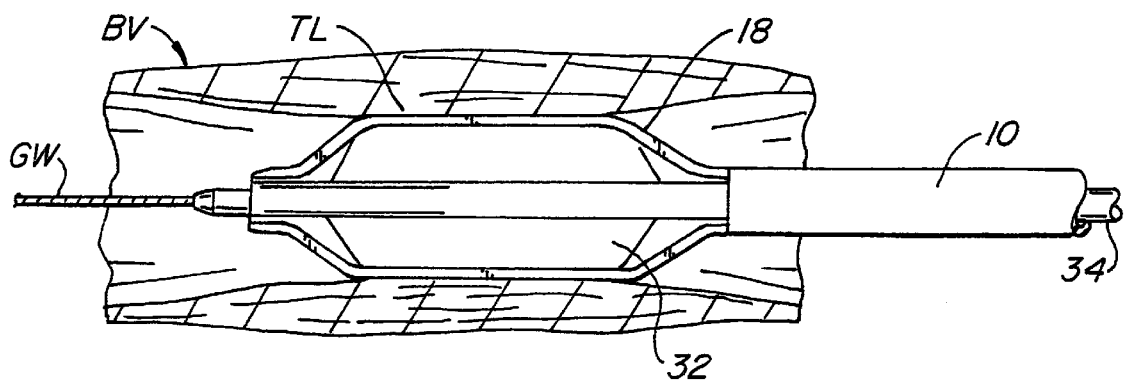

Referring to FIGS. 13–15, an exemplary method for performing angioplasty using RESC 10 and the balloon catheter 34 will be described. Initially, an incision is made in the femoral artery using the Seldinger procedure. A guide catheter is then inserted through an introducer sheath over a first guide wire up to a coronary ostium in the conventional manner. A second guidewire GW is then introduced through the guide catheter until reaching a target location TL in a blood vessel BV in the conventional manner. Balloon catheter 34 is then advanced over the guidewire GW to the target location TL where balloon 32 is inflated to perform angioplasty in the conventional manner.

The RESC 10 will preferably be loaded on the balloon catheter 34 following the primary angioplasty procedure in order to minimize the dwell time of the RESC 10 in the vasculature, although in some cases the RESC 10 may be preloaded on the balloon catheter prior to the primary angioplasty procedure. Thus, following the primary angioplasty procedure, with the guidewire GW remaining in place, the angioplasty catheter is fully withdrawn from the patient. RESC 10, with its primary shielding (not shown) still in place, is then loaded on the balloon catheter by inserting the distal end of the balloon catheter in opening 24 of RESC 10. Following the removal of the primary shielding, both catheters are rapidly introduced into the patient's vasculature through the guide catheter, preferably with the balloon catheter 34 leading, so that the balloon catheter 34 reaches the target location TL in the blood vessel BV over the guide wire GW in a generally conventional manner as shown in FIG. 13.

The use of a movable secondary shielding arrangement over the radioactive portion of the RESC 10 or a shielded guide catheter may not be practical due to the substantial shield thickness needed to provide significant or even adequate shielding when using either β or γ radiation, and the human vasculature will generally not accommodate such increases in hardware size. Therefore, it is important that traversing the RESC 10 to the treatment region be done in a rapid manner and that the radiation emitting portion of the catheter be kept in motion at all times except during the therapy period, to minimize the patient's exposure to unwanted radiation.

After the balloon catheter 34 is positioned at the target location TL by fluoroscopic observation (with balloon 32 still deflated), RESC 10 is advanced distally as shown in FIG. 14 until the distal region 18 is fluoroscopically aligned over balloon 32. Fluoroscopic alignment will preferably proceed according to one of the alignment schemes previously described in connection with FIGS. 2, 5, and 6.

After positioning has been achieved, balloon 32 is again inflated, engaging distal region 18 of the RESC 10 against the wall of the blood vessel BV by urging elements 30 into engagement with the vessel wall as shown in FIG. 15. Depending on the type of radioactive material and its activation level, the balloon 32 will remain inflated for about 1 to 3 minutes, usually 2 to 3 minutes. In other cases, the balloon may remain inflated for up to about 30 minutes. RESC 10 can be provided with a perfusion lumen as described in co-pending U.S. Pat. application Ser. No.

08/401,541 (Attorney Docket No. 15509-7-2), previously incorporated by reference, to allow blood to flow through the vessel for treatments times exceeding about 3 minutes. Optionally, a drug or an agent can be delivered to the target location TL during the irradiation procedure as previously described.

After irradiation, the balloon 32 is deflated and the RESC 10 and the balloon catheter 34 are rapidly withdrawn from the patient and the primary shield is re-positioned over the radiation emitting portion of RESC 10 to contribute to the safety of the procedure, both for the patient and the catheterization laboratory personnel.

Although the foregoing invention has been described in some detail by way of illustration and example, for purposes of clarity of understanding, it will be obvious that certain changes and modifications may be practiced within the scope of the appended claims.

What is claimed is:

1. A radiation-emitting device adapted for use in combination with a balloon catheter having a balloon at a distal end said device comprising:

structure which is adapted to be removably securable over the balloon and expansible upon balloon inflation, and wherein the balloon-securable structure is collapsible upon balloon deflation; and a radioactive source on or within the balloon-securable structure.

2. A device as in claim 1, wherein the radioactive source comprises a radioisotope selected from the group consisting of $^{192}$Iridium, $^{90}$Yttrium, $^{90}$Strontium, and $^{125}$Iodine.

3. A device as in claim 1, wherein the radioactive source comprises a plurality of discrete elements, and further comprising a means for uniformly aligning the discrete elements over the balloon when the balloon is inflated.

4. A device as in claim 3, wherein said discrete elements are integrally formed within the aligning means.

5. A device as in claim 1, wherein the radioactive source comprises a solid substance.

6. A device as in claim 5, wherein the solid comprises a plurality of elongate elements.

7. A device as in claim 1, wherein the structure comprises a radially expansible sleeve having an internal lumen for receiving the balloon.

8. A device as in claim 7, wherein the sleeve is axially split to permit radial expansion.

9. A device as in claim 7, wherein the sleeve is formed at least partially of an elastomeric material to permit radial expansion.

10. A device as in claim 7, wherein the sleeve is formed at least partially from a mesh which permits radial expansion.

11. A device as in claim 7, wherein the sleeve is folded to permit radial expansion.

12. A device as in claim 7, further comprising an elastomeric tube around the sleeve.

13. A device as in claim 7, wherein the sleeve is slideably received over the balloon.

14. A device as in claim 3, wherein the discrete elements become radiopaque upon absorption of X-radiation from a fluoroscope to permit fluoroscopic imaging of the discrete elements.

15. A device as in claim 1, further comprising at least one radiopaque marker on the structure.

16. A radiation-emitting sleeve catheter system comprising:

a shaft having a proximal end and a distal end;

a radially expansible and collapsible sleeve disposed at the distal end of the shaft, said sleeve having an internal lumen for receiving a balloon on a balloon catheter to allow the sleeve to be expanded upon balloon inflation and to be collapsed upon balloon deflation; and a radioactive source secured to the radially expansible sleeve.

17. A radiation-emitting sleeve catheter system as in claim 16, wherein the radioactive source is integrally formed within the sleeve.

18. A radiation-emitting sleeve catheter system as in claim 16, wherein the radioactive source comprises a plurality of elongate elements that are substantially uniformly distributed over the sleeve when the balloon is inflated therein.

19. A radiation-emitting sleeve catheter system as in claim 18, wherein the elements are axially aligned with the internal lumen.

20. A radiation-emitting sleeve catheter system as in claim 19, wherein the elements each have a length in the range from 15 mm to 45 mm.

21. A radiation-emitting sleeve catheter system as in claim 16, wherein the radially expansible sleeve further includes at least one perfusion lumen for providing blood flow past the balloon when inflated.

22. A radiation-emitting sleeve catheter system as in claim 16, further comprising a therapeutic drug included in the sleeve.

23. A radiation-emitting sleeve catheter system as in claim 16, wherein the sleeve includes a side port for introducing the balloon.

24. A radiation-emitting sleeve catheter system as in claim 16, wherein the shaft comprises a rod at least partially surrounded by a polymer tube.

25. A radiation-emitting sleeve catheter system as in claim 18, wherein the discrete elements become radiopaque upon absorption of X-radiation from a fluoroscope to permit fluoroscopic imaging of the discrete elements.

26. A radiation-emitting sleeve catheter system as in claim 16, further comprising at least one radiopaque marker on the expansible sleeve.

27. A method for performing angioplasty, said method comprising:

inflating a balloon attached to a shaft within a stenosed region of a blood vessel to produce a treated region;

deflating the balloon;

placing a radioactive source over the deflated balloon; and reinflating the balloon to engage the radioactive source against or in close proximity to the blood vessel wall within the treated region.

28. A method as in claim 27, further comprising delivering a dose of from about 6 Gy to 20 Gy at the treated region with the radioactive source.

29. A method as in claim 28, further comprising maintaining the radioactive source in the treated region for a period from 1 minute to 40 minutes.

30. A method as in claim 27, further comprising providing blood flow past the reinflated balloon.

31. A method as in claim 27, wherein the placing step comprises placing a radially expansible sleeve over the deflated balloon, wherein the sleeve includes the radioactive source.

32. A method as in claim 31, wherein the placing step further comprises withdrawing the deflated balloon from the blood vessel, placing the sleeve over the balloon shaft while outside of the blood vessel, and reintroducing the deflated balloon to the treated region of the blood vessel.

33. A method as in claim 32, wherein the placing step further comprises advancing the sleeve over the shaft until the sleeve is aligned over the balloon.

34. A method as in claim 32, further comprising performing the withdrawing and the reintroducing steps with the assistance of a guidewire.

35. A method as in claim 32, further comprising rapidly advancing the deflated balloon and the sleeve over the guidewire to reintroduce the balloon.

36. A method as in claim 27, further comprising delivering a drug to the treated region.

37. A method as in claim 31, further comprising positioning an elastomeric tube over the radially expansible sleeve, wherein the tube facilitates a uniform collapse of the radioactive source after balloon deflation.

* * * * *